United States Patent
Jun et al.

(10) Patent No.: US 7,963,147 B2
(45) Date of Patent: Jun. 21, 2011

(54) MICRO GAS SENSOR AND METHOD FOR MANUFACTURING THE SAME

(75) Inventors: Chi-Hoon Jun, Daejon (KR);
Sang-Choon Ko, Daejon (KR);
Hyeon-Bong Pyo, Daejon (KR);
Seon-Hee Park, Daejon (KR)

(73) Assignee: Electronics and Telecommunications Research Institute, Daejon (KR)

( * ) Notice: Subject to any disclaimer, the term of this patent is extended or adjusted under 35 U.S.C. 154(b) by 201 days.

(21) Appl. No.: 11/951,986

(22) Filed: Dec. 6, 2007

(65) Prior Publication Data

US 2008/0134753 A1 Jun. 12, 2008

(30) Foreign Application Priority Data

Dec. 7, 2006 (KR) .................... 10-2006-0123686

(51) Int. Cl.
*G01N 7/00* (2006.01)
*G01N 27/12* (2006.01)
(52) U.S. Cl. ............... 73/31.06; 73/25.01; 73/25.05
(58) Field of Classification Search ............. 73/31.05, 73/31.06, 25.01, 25.05; 204/408, 242
See application file for complete search history.

(56) References Cited

U.S. PATENT DOCUMENTS

| | | | |
|---|---|---|---|
| 4,849,050 A * | 7/1989 | Evans et al. | ............ 438/53 |
| 5,019,885 A | 5/1991 | Yagawara et al. | |
| 5,907,765 A * | 5/1999 | Lescouzeres et al. | ...... 438/49 |
| 6,161,421 A | 12/2000 | Fang et al. | |
| 6,582,987 B2 * | 6/2003 | Jun et al. | ............ 438/49 |
| 6,896,780 B2 * | 5/2005 | Yang et al. | ........... 204/408 |
| 6,906,392 B2 * | 6/2005 | Benzel et al. | ........... 257/414 |
| 7,276,745 B2 | 10/2007 | Nakagawa et al. | |
| 2008/0264146 A1 * | 10/2008 | Roesch et al. | ........... 73/23.33 |
| 2009/0151429 A1 * | 6/2009 | Jun et al. | ........... 73/31.06 |

FOREIGN PATENT DOCUMENTS

| | | |
|---|---|---|
| JP | 62095454 | 5/1987 |
| JP | 07-092123 | 4/1995 |
| JP | 2002-286675 | 10/2002 |
| KR | 2001-0019419 A | 3/2001 |
| KR | 2006-0076922 A | 7/2006 |
| WO | WO2006077197 A1 * | 7/2006 |

OTHER PUBLICATIONS

"Micromechanical Devices and Fabrication." S. F. Bart and M. W. Judy (ed.). Wiley Encyclopedia of Electrical and Electronics Engineering. 1999. pp. 648-655.*

(Continued)

*Primary Examiner* — Lisa M Caputo
*Assistant Examiner* — Punam Roy
(74) *Attorney, Agent, or Firm* — Rabin & Berdo, P.C.

(57) ABSTRACT

Provided are a micro gas sensor for measuring a gas concentration configured to achieve a high heating and cooling rate of a gas sensitive layer, achieve temperature uniformity, and achieve durability against thermal impact and mechanical impact; and a method for manufacturing the micro gas sensor. The micro gas sensor includes: a vacuum cavity disposed in a substrate; a support layer covering the vacuum cavity; a sealing layer sealing the support layer and the vacuum cavity; a micro heater disposed on the sealing layer; a plurality of electrodes disposed on the micro heater, insulated from the micro heater; and a gas sensitive layer covering the electrodes.

24 Claims, 11 Drawing Sheets

OTHER PUBLICATIONS

"Resistance Heating." J. Spannhake, A. Helwig, A. Friedberger, G. Muller, W. Hellmich (ed.). Wiley Encyclopedia of Electrical and Electronics Engineering. Posted Online Jun. 15, 2007. pp. 1-12.*

C. Liu and Y.-C. Tai. "Sealing of Micromachined Cavities Using Chemical Vapor Deposition Methods: Characterization and Optimization." IEEE Journal of Microelectromechanical Systems. vol. 8. No. 2. Jun. 1999. pp. 135-145.*

* cited by examiner (a)

MICRO GAS SENSOR AND METHOD FOR MANUFACTURING THE SAME

BACKGROUND OF THE INVENTION

1. Field of the Invention

The present invention relates to a gas sensor; and, more particularly, to a micro gas sensor for measuring a gas concentration, and a method for manufacturing the same.

This work was supported by the IT R & D program of the MIC/IITA [2006-S-007-01, "Ubiquitous Health Monitoring Module and System Development"].

2. Description of Related Art

As interests on the environment for the future increase, development of a miniature sensor is increasingly demanded, which can obtain precise and various information within a short period of time. Particularly, to form a pleasant housing environment, cope with harmful industrial environments, and manage food materials and grocery producing processes, efforts are being made to achieve miniaturization, high precision and low price of a gas sensor that facilitates measuring of a concentration of associated gases.

Currently, due to the development of a semiconductor manufacturing technology, the gas sensor is gradually evolving from a typical ceramic sintering or a thick film type structure into a microelectromechanical (MEMS) micro gas sensor.

A measuring method of the micro gas sensor, which is most widely used, is to measure electrical-characteristic changes of a gas sensitive layer when a gas is absorbed to the gas sensitive layer. In general, metal oxide such as $SnO_2$ is used for the gas sensitive layer, and changes in electrical conductivity according to a concentration of a target gas are measured, which is relatively simple.

When the gas sensitive layer of metal oxide is heated to a high temperature, the changes in a measured value are more notable. Accordingly, temperature control is necessary for fast and precise measurement of the gas concentration. Also, before the gas concentration is measured, gas species and moisture absorbed to the gas sensitive layer are removed by heating to a high temperature so as to reset the gas sensitive layer to an initial state.

In the gas sensor, temperature characteristic directly affects critical measurement factors of the gas sensor such as measurement sensitivity, reset time, and reaction time of the sensor. Thus, a micro heater is effective for efficient heating, which locally and uniformly heats only the gas sensitive layer.

However, in the case of the micro gas sensor, if a large amount of power is consumed in controlling a temperature, a large battery or power supply source is required, and thus the entire size of a measuring system is increased even if the volume of the sensor and a measuring circuit is small. For this reason, to implement the micro gas sensor, a structure resulting in low power consumption must be considered primarily.

In most known manufacturing processes for the micro gas sensor, a silicon substrate having very high thermal conductivity is mainly used. In order to reduce heat loss, an etched pit or a groove is formed in a sensor structure through a bulk micromachining process to form a structure such as a membrane, a cantilever, or a bridge suspended from the substrate, and then a micro heater, an insulation layer, and a gas sensitive layer are sequentially formed on the structure.

However, the structure such as the membrane, the cantilever, or the bridge cannot remove the air existing within the structure, and thus there is a limitation in reducing the heat loss. Also, since the micro gas sensor is formed mainly through substrate etching, there is a limitation in miniaturizing a sensor device, and it is difficult to apply a standard complementary metal oxide semiconductor (CMOS).

Also, even if the micro gas sensor having the afore-mentioned structure has a suspended structure, the micro gas sensor includes an open cavity opened in one direction and having a large height difference. This causes inflow of dust particles or disturbs flow around the sensor due to the large height difference, and thus a measured value becomes inaccurate.

For commercialization, the micro gas sensor must be reliably driven for about two to three years. This condition is very strict for the gas sensor that undergoes repetitive heating and cooling within a temperature range between approximately 100° C. and 600° C. by the micro heater. An issue in this repetitive heating and cooling process is damaged by thermal stress from a temperature gradient applied to a sensor structure suspended from the substrate and mechanical impact.

In a conventional method to solve this issue, a base support layer of the suspended structure is formed as a single layer of silicon oxide ($SiO_2$) or silicon nitride ($Si_3N_4$), or a stacked layer or multiple layers of three or more layers having different thicknesses, such as $Si_3N_4/SiO_2$, $SiO_2/Si_3N_4$, $Si_3N_4/SiO_2/Si_3N_4$, or $SiO_2/Si_3N_4/SiO_2$ to achieve stress balance. Then, a micro heater, a sensing electrode, and a gas sensitive layer are sequentially patterned thereon to improve structural brittleness.

However, even if the stress balance is achieved, structural safety cannot be ensured when the temperature non-uniformity increases on the heated suspended structure because those materials are insulator materials having high brittleness and low thermal conductivity. Accordingly, the durability of the micro gas sensor is associated with the constituent material of the structure, and a design of the micro heater.

As mentioned above, although many researches have been conducted on the micro gas sensor, the conventional micro gas sensor still needs to be improved with regard to thermal insulation, power consumption, temperature uniformity, measurement precision, durability, and size.

SUMMARY OF THE INVENTION

An embodiment of the present invention is directed to providing a micro gas sensor configured to achieve low power consumption, and a method for manufacturing the same.

Another embodiment of the present invention is directed to providing a micro gas sensor configured to achieve a high heating and cooling rate of a gas sensitive layer, and a method for manufacturing the same.

Another embodiment of the present invention is directed to providing a micro gas sensor configured to achieve temperature uniformity, and a method for manufacturing the same.

Another embodiment of the present invention is directed to providing a micro gas sensor configured to achieve durability against mechanical impact applied from the outside and thermal impact, and a method for manufacturing the same.

Another embodiment of the present invention is directed to providing a micro gas senor configured to achieve high measurement precision by minimizing a height difference so that the micro gas sensor is not affected by dust particles flowing into a micro gas sensor structure, or flow therearound is not disturbed, and a method for manufacturing the same Another embodiment of the present invention is directed to providing a micro gas sensor configured to achieve miniaturization, low cost, and mass production through a semiconductor batch process, and a method for manufacturing the same.

In accordance with an aspect of the present invention, there is provided a micro gas sensor, which includes: a vacuum cavity disposed in a substrate; a support layer covering the vacuum cavity; a sealing layer sealing the support layer and the vacuum cavity; a micro heater disposed on the sealing layer; a plurality of electrodes disposed on the micro heater, insulated from the micro heater; and a gas sensitive layer covering the electrodes.

In accordance with another aspect of the present invention, there is provided a micro gas sensor which includes: a vacuum cavity disposed in a substrate; a support layer covering the vacuum cavity; a sealing layer sealing the support layer and the vacuum cavity; a micro heater formed on the sealing layer; a plurality of electrodes insulated from the micro heater and formed on the same plane; and a gas sensitive layer covering the micro heater and the electrodes.

In accordance with another aspect of the present invention, there is provided a method for manufacturing a micro gas sensor, which includes the steps of: a) forming a cavity in a substrate; b) forming a support layer on the cavity; c) forming a sealing layer on the substrate including the support layer to seal the cavity in a vacuum state; d) forming a micro heater and a plurality of electrodes on the sealing layer, the micro heater and the electrodes being insulated from each other; and e) forming a gas sensitive layer on the micro heater and the electrodes.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

DESCRIPTION OF SPECIFIC EMBODIMENTS

Figure 1A:
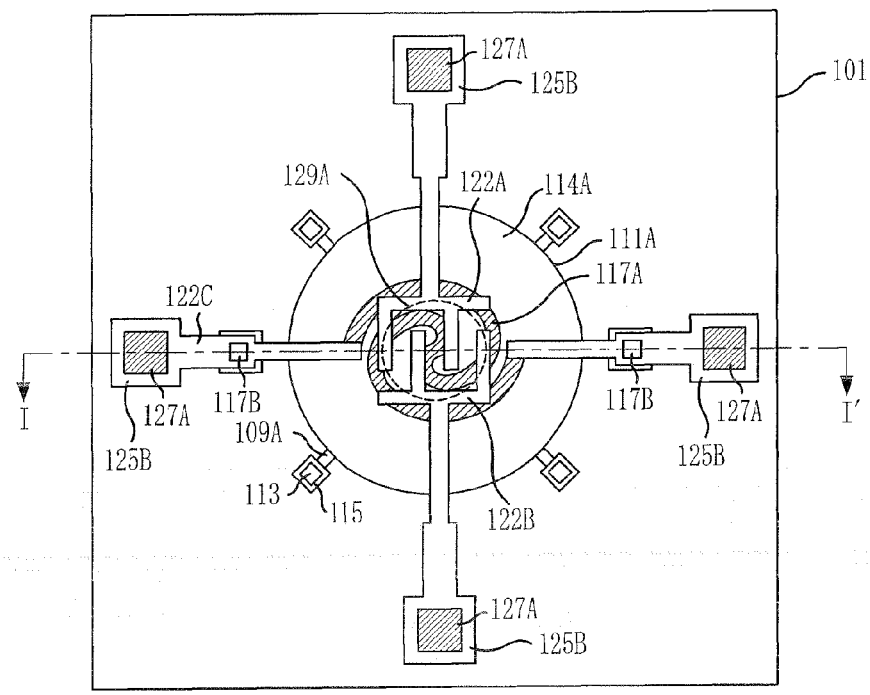
FIG. 1A is a plane view of a micro gas sensor in accordance with a first embodiment of the present invention.

The advantages, features and aspects of the invention will become apparent from the following description of the embodiments with reference to the accompanying drawings, which is set forth hereinafter. In the drawings, the dimensions of layers and regions are exaggerated for clarity of illustration. It will be understood that when a layer (or film) is referred to as being "on" another layer or substrate, it can be directly on the other layer or substrate, or intervening layers may also be present. Like reference numerals refer to like elements throughout the drawings.

Embodiment 1

Figure 1B:
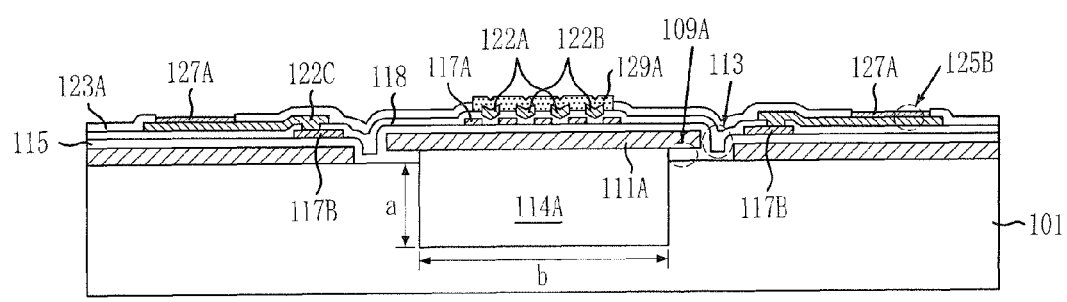
FIG. 1B is a cross-sectional view taken along line I-I' of FIG. 1A.

FIG. 1A is a plane view of a micro gas sensor in accordance with a first embodiment of the present invention, and FIG. 1B is a cross-sectional view taken along line I-I' of FIG. 1A.

Referring to FIGS. 1A and 1B, the micro gas sensor in accordance with the first embodiment of the present invention includes a vacuum cavity buried in a silicon substrate 101 to minimize heat loss. The vacuum cavity 114A is sealed in a vacuum state by a sealing layer 115, and has a plane structure with a random shape such as a circle, a semicircle, an oval, a lozenge, a parallelogram, a trapezoid, a triangle, a quadrangle, a hexagon, and an octagon. The vacuum cavity 114A has a diameter (b), a surface dimension, or a width ranging from approximately 1 μm to approximately 10 mm on a plane, and has a depth (a) ranging from approximately 1 μm to hundreds of micrometers, preferably approximately 1 μm to approximately 900 μm, from an upper portion of the silicon substrate 101.

The micro gas sensor in accordance with the first embodiment of the present invention further includes a support layer 111A covering the vacuum cavity 114A to provide durability and temperature uniformity. The support layer 111A may be formed of polysilicon. Because of structural characteristics of the micro gas sensor, thermal stress is inevitably caused because of temperature non-uniformity when a suspended sensor structure is repetitively heated and cooled by a micro heater 117A.

Also, the micro gas sensor is greatly affected by external mechanical impact. Therefore, by forming the support layer 111A of polysilicon, the micro gas sensor is provided with durability against thermal impact and mechanical impact. The support layer 111A formed using the polysilicon layer also serves as a heat spreader that achieves temperature uniformity in heating of the micro heater 117A. This is because the polysilicon layer is excellent in modulus of elasticity and thermal conductivity, compared to a single layer of a silicon oxide ($SiO_2$) layer or a silicon nitride ($Si_3N_4$) layer, or a stacked layer or a multi-layer of layers having different thicknesses such as $Si_3N_4/SiO_2$, $SiO_2/Si_3N_4$, $Si_3N_4/SiO_2/Si_3N_4$, and $SiO_2/Si_3N_5/SiO_2$, which is used as a base support layer and has brittleness and low thermal conductivity.

As the modulus of elasticity is greater, a structural mechanical restoring force increases. Also, as the thermal conductivity is higher, the temperature non-uniformity decreases and thus thermal stress also decreases.

The vacuum cavity 114A and the support layer 111A improve thermal insulation between the micro heater 117A and the silicon substrate 101 to be formed later, and ensure the temperature uniformity, measurement precision, and durability of the micro gas sensor structure. Also, since the vacuum cavity 114A is sealed flat by the sealing layer 115, and thus a height difference is minimized, an upper surface is two-dimensionally formed. Accordingly, inflow of dust particles is prevented, and laminar flow around the structure is ensured, thereby improving measurement precision of the micro gas sensor.

Also, the micro gas sensor in accordance with the first embodiment further includes the micro heater 117A. The micro heater 117A is formed on the sealing layer 115 corresponding to the support layer 111A, separated from the support layer 111A by the sealing layer 115. The micro heater 117A may have a circular shape, but the micro heater 117A is not limited to the circular shape, and may have a variety of shapes. The micro heater 117A may be formed of a doped polysilicon layer. This is because compatibility with a general semiconductor manufacturing process can be provided while thermal durability against high-temperature heating required by the micro gas sensor can be ensured.

Since the vacuum cavity 114A is disposed between the micro heater 117A and the silicon substrate 101, heat loss to a lower portion of the silicon substrate 101 can be greatly reduced, and a gas sensitive layer 129A (to be described later) can be heated to a high temperature even though a low voltage or current is applied to the micro heater 117A. Also, since thermal mass of the structure decreases, the gas sensitive layer 129A can be heated or cooled rapidly. Also, as the width or depth of the vacuum cavity 114A is wider or deeper, relative to the size of the micro heater 117A, the heat loss decreases.

Also, the micro gas sensor in accordance with the first embodiment of the present invention further includes a pair of electrodes 122A and 122B on an interlayer dielectric layer 118 covering the micro heater 117A. The electrodes 122A and 122B are separated from each other, and overlap the micro heater 117A. The electrodes 122A and 122B have an interdigitated array structure, each having at least one branching finger. Each of the electrodes 122A and 122B has a quadrangular or circular comb shape. However, the pair of electrodes 122A and 122B separated from each other are not limited to the aforementioned specific shape.

The micro gas sensor in accordance with the first embodiment of the present invention further includes the gas sensitive layer 129A covering the pair of separated electrodes 122A and 122B. The gas sensitive layer 129A is formed of metal oxide such as $SnO_2$, $ZnO$, $WO_3$, $In_2O_3$, $Ga_2O_3$, $Fe_2O_3$, $TiO_2$, $NiO$, and $MoO_3$, or of a doped thin film of the metal oxide.

Besides, any thin film material that undergoes a change in electrical characteristic according to the gas concentration can be used for the gas sensitive layer 129A. For example, examples of the thin film material include a nanotube or nanowire of carbon, silicon, or metal, or an array thereof. The thin film material is not limited to a specific material, and may be any one of metal oxide, metal and semiconductor, and a mixture thereof.

The micro gas sensor in accordance with the first embodiment further includes metallization lines 122C to connect the micro heater 117A to an external wire. The metallization line 122C is formed simultaneously with the pair of separated electrodes 122A and 122B by using the same material.

Figure 3A:
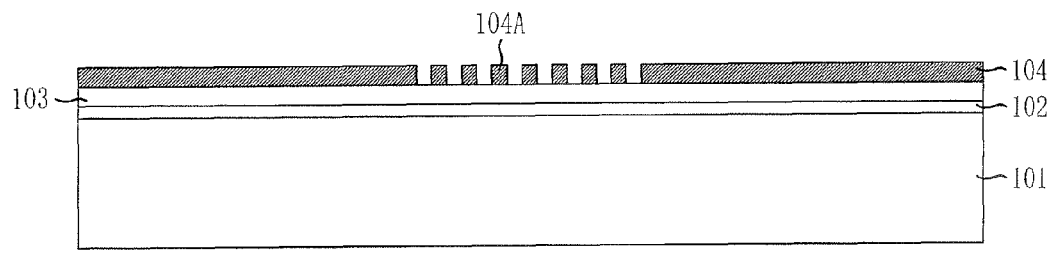
FIGS. 3A to 3R are cross-sectional views of a method for manufacturing the micro gas sensor in accordance with the first embodiment of the present invention.
Figure 3B:
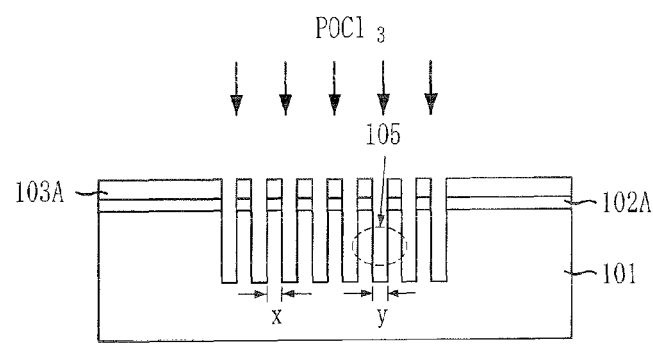
Figure 3C:
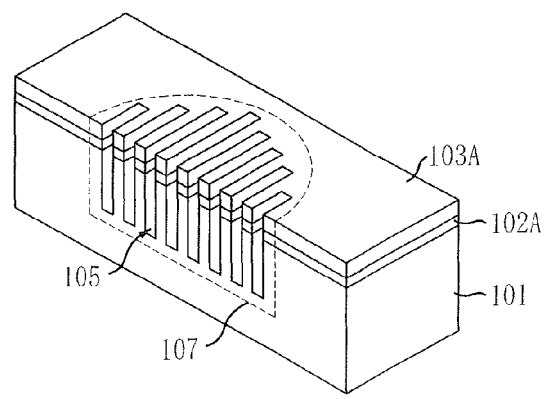
Figure 3D:
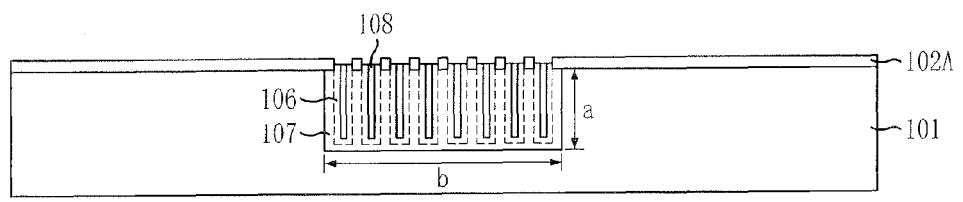
Figure 3E:
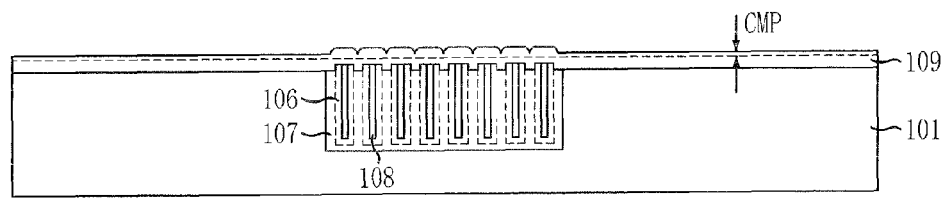
Figure 3F:
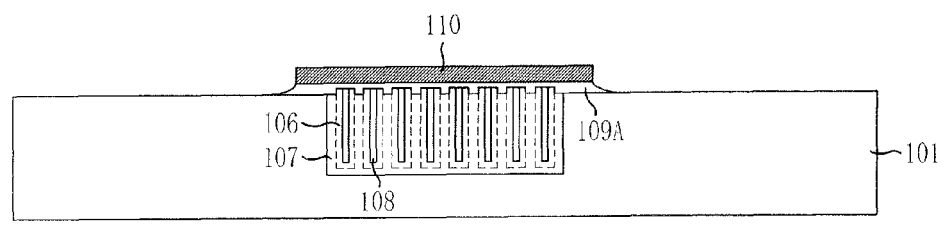
Figure 3G:
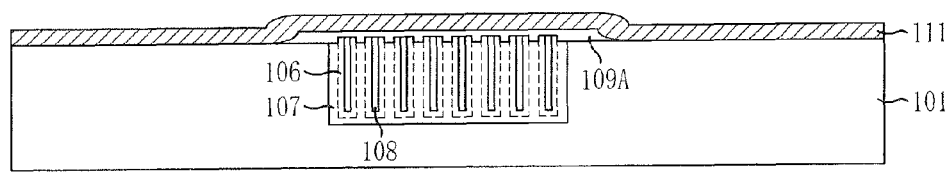
Figure 3H:
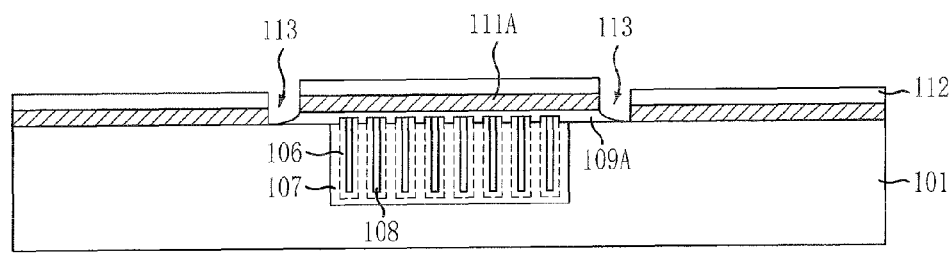
Figure 3I:
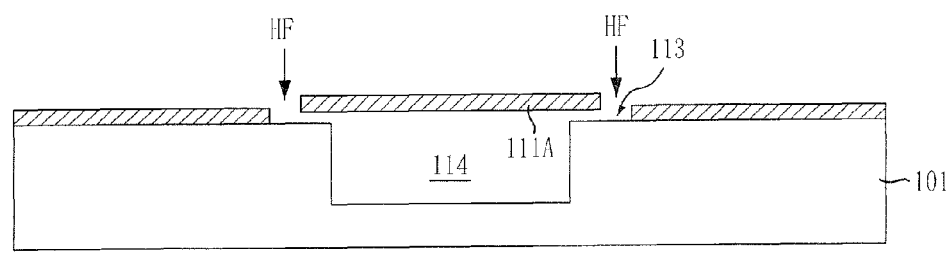
Figure 3J:
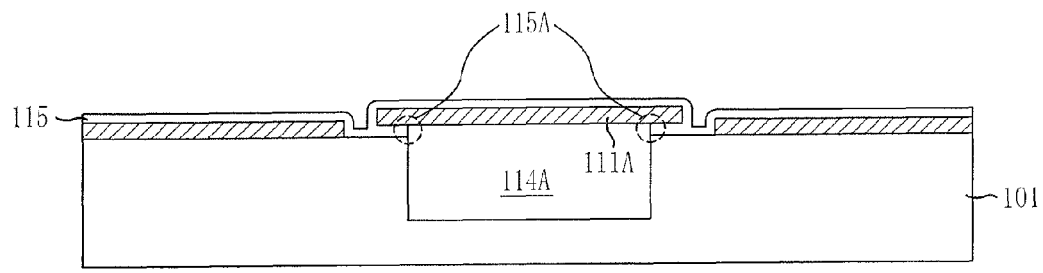
Figure 3K:
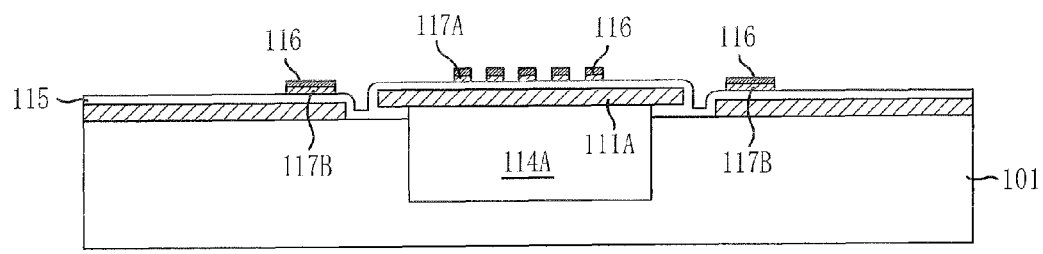
Figure 3L:
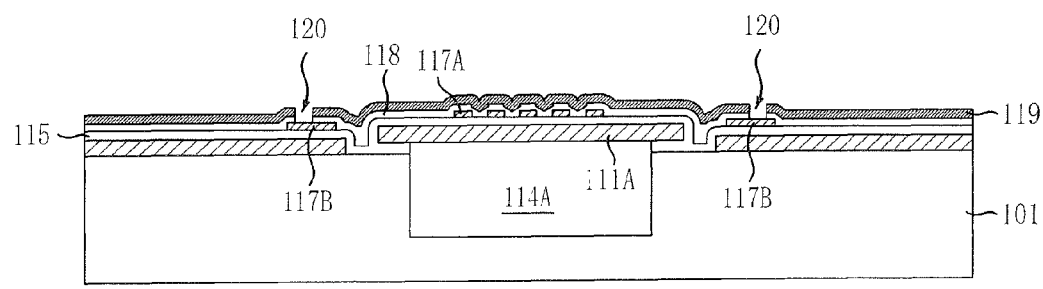
Figure 3M:
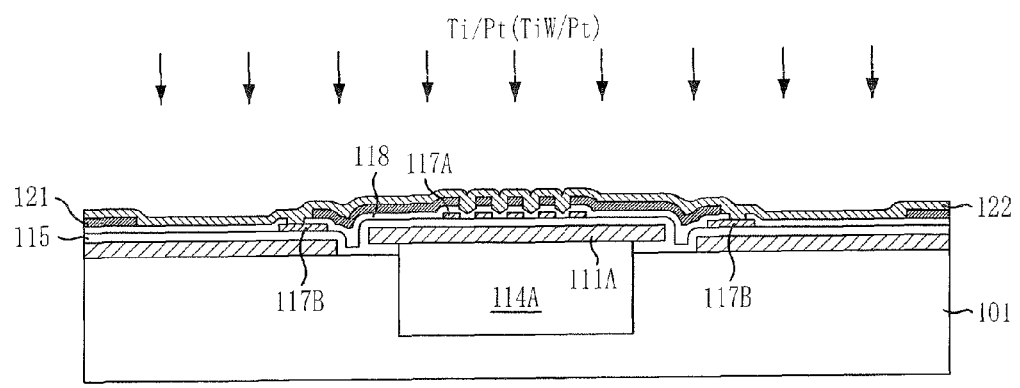
Figure 3N:
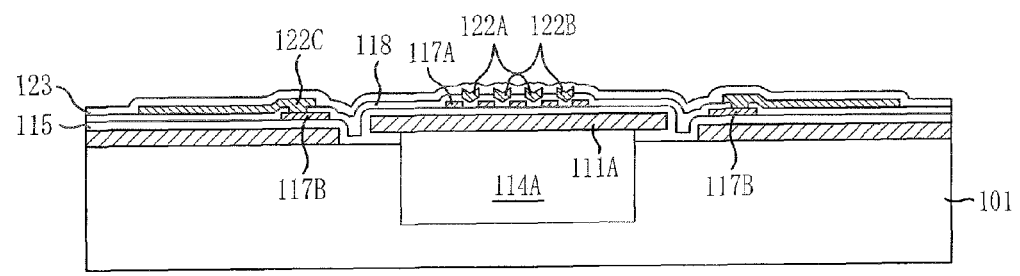
Figure 3O:
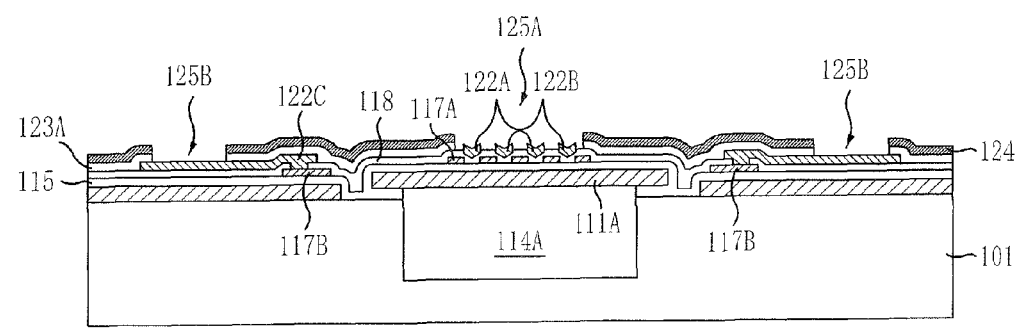
Figure 3P:
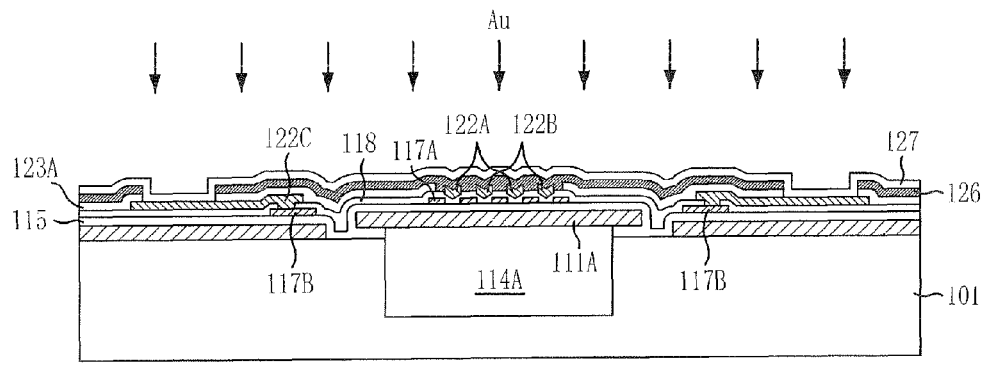
Figure 3Q:
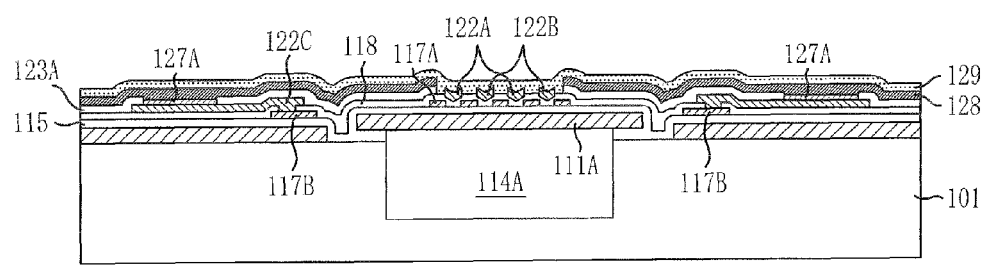
Figure 3R:
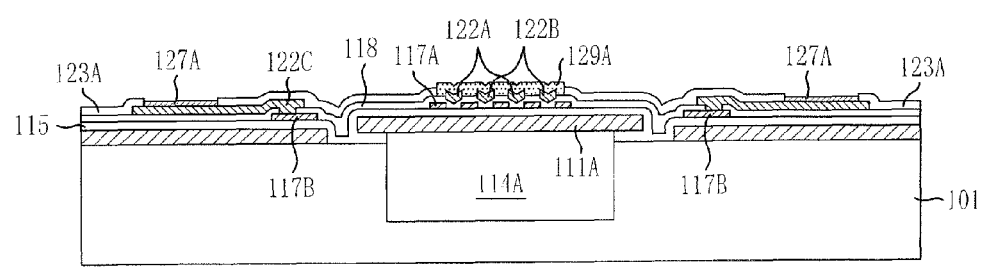

FIGS. 3A to 3R are cross-sectional views sequentially showing a method for manufacturing the micro gas sensor of FIGS. 1A and 1B in accordance with the first embodiment of the present invention.

Referring to 3A, a $Si_3N_4$ layer 102 and a $SiO_2$ layer 103 are sequentially deposited on a silicon substrate 101. The $Si_3N_4$ layer 102 and the $SiO_2$ layer 103 serve as a mask layer for protecting the substrate during a subsequent etching process, and are deposited by using a low pressure chemical vapor deposition (LPCVD) method or a plasma enhanced chemical vapor deposition (PECVD) method.

The $Si_3N_4$ layer 102 is deposited with a thickness ranging from approximately 1000 Å to approximately 1400 Å, preferably approximately 1200 Å. The $SiO_2$ layer 103 is deposited with a thickness of at least 6000 Å, preferably from approximately 6000 Å to approximately 10000 Å.

Thereafter, a photoresist layer 104 is applied on the $SiO_2$ layer 103, and exposure and development processes are performed by using a photo mask to form fine line-width portions 104A. The photo mask has a shape where a plurality of trench patterns are transferred to a region in which a cavity is to be formed. The trench shapes may form a bar pattern as shown in the drawing, or may form an island pattern at regular intervals.

As shown in FIGS. 3B and 3C, an etching process is performed by using the photoresist layer 104 having the fine line-width portions 104A as an etch mask to etch the $SiO_2$ layer 103 and the $Si_3N_4$ layer 102 serving as a mask layer. The etching process is a dry etching process.

Thus, an $SiO_2$ layer pattern 103A and a $Si_3N_4$ layer pattern 102A having the same pattern as that of the fine line-width portions 104A of the photoresist layer 104 are formed in a region 107 where a cavity is to be formed. Thereafter, a strip process is performed to remove the photoresist layer 104.

Then, an etching process is performed by using the $SiO_2$ layer pattern 103A and the $Si_3N_4$ layer pattern 102A as an etch mask to etch the silicon substrate 101 exposed from the $SiO_2$ layer pattern 103A and the $Si_3N_4$ layer pattern 102A. Accordingly, a plurality of trenches 105 are formed in the silicon substrate 101 corresponding to the region 107 where the cavity is to be formed. The etching process is a dry etching process using a reactive ion etching (RIE) method or a deep-RIE method. Also, the trenches 105 are formed to have a depth (a in FIGS. 1 and 2) between approximately 1 μm to hundreds of micrometers. A ratio between a line-width (y) of the trench 105 and a distance (x) between adjacent trenches 105 are properly adjusted in due consideration of a subsequent process of forming fine pores in a trench thermal $SiO_2$ layer to be formed later.

Thereafter, the silicon substrate 101 is $n^+$-doped by diffusing $POCl_3$ in a furnace at a temperature ranging from approximately 850° C. to approximately 950° C., preferably 900° C. for about 20 minutes to about 40 minutes, preferably for 30 minutes. This process is performed in order to speed up thermal oxidation in a subsequent thermal oxidation process on the trenches 105, and to facilitate removal of the trench thermal $SiO_2$ layer including phosphorus (P) with a wet etching solution or a dry etching gas.

Thereafter, referring to FIG. 3D, a wet etching process is performed by using a buffered hydrogen fluoride (BHF) solution to remove the $SiO_2$ layer pattern 103A and etching residues remaining in the dry etching process such as the RIE performed to form the trenches 105.

Thereafter, an oxidation process is performed on the $Si_3N_4$ layer pattern 102A by using an oxidation mask to form a thermal $SiO_2$ layer 106 on an inner surface of the $n^+$ doped trench 105. The oxidation process uses a furnace, and is performed at a temperature ranging from approximately 900° C. to approximately 1000° C. in $O_2$ or $H_2/O_2$ atmosphere, thereby converting the inner surface of the trench 105 including phosphorus (P) into the thermal $SiO_2$ layer 106.

Thus, the region 107 is defined, in which a cavity with a surface dimension or a diameter (b of FIGS. 1 and 2) ranging from 1 μm to a few mm is to be formed. During the oxidation process, fine pores 108 having a width ranging from approximately 0.1 μm to approximately 0.3 μm are simultaneously formed in the thermal $SiO_2$ layer 106. The fine pores 108 serve as micro capillaries contributing to better infiltration of a wet etching solution or a process gas for gas phase etching in a subsequent process of removing the thermal $SiO_2$ layer 107.

Referring to FIG. 3E, the $Si_3N_4$ layer pattern 102A is removed by using a phosphoric acid ($H_3PO_4$) solution.

Thereafter, a low-temperature silicon oxide (LTO) layer 109 is deposited with a thickness ranging from approximately 5500 Å to approximately 6500 Å, preferably approximately 6000 Å by using an LPCVD method.

Thereafter, a planarization process is performed on the LTO layer 109 by a chemical mechanical polishing (CMP) method to polish the LTO layer 109. In the drawing, the CMP process is performed up to a portion indicated by a dotted line.

Then, referring to FIG. 3F, a photoresist layer is applied on the silicon substrate 101, and exposure and development processes using a photo mask are performed to form a photoresist pattern 110 in order to form an etching passage 109A for removing the thermal $SiO_2$ layer 106 formed in the region 107 where the cavity is to be formed. The photoresist pattern 110 is formed to sufficiently cover the region 107 where the cavity is to be formed.

Thereafter, a wet etching process is performed by using the photoresist pattern 110 defining a portion to become the etching passage 109A as an etch mask to etch the LTO layer 109. Thus, the etching passage 109A branching outwardly from edges of the region 107 where the cavity is to be formed is formed.

Referring to FIG. 3G, a strip process is performed to remove the photoresist pattern 110. Thereafter, a washing process may be performed.

Then, a polysilicon layer 111 serving as a support layer is formed along a height difference on the silicon substrate 101 including the etching passage 109A. The polysilicon layer 111 is formed with a thickness ranging from approximately 1 μm to approximately 20 μm by using an LPCVD method or an epi-poly deposition method. The polysilicon layer 111 may be formed as a single layer, a stacked layer or multi-layers with divided thicknesses.

Thereafter, post-annealing is performed in a furnace at a temperature ranging from approximately 900° C. to approximately 1100° C., preferably 1000° C. in $N_2$ atmosphere for about 90 minutes to about 150 minutes, preferably, 120 minutes, thereby releasing compression stress applied to the polysilicon layer 111.

Referring to FIG. 3H, a photoresist layer is applied on the polysilicon layer 111, and exposure and development processes are performed using a photo mask to form a photoresist pattern 112. The photoresist pattern 112 has a structure opened at a portion corresponding to an etching hole 113 that serves as an inlet of a wet etching solution or a gas phase etching gas used in removing the trench thermal $SiO_2$ layer 106 and the LTO layer of the etching passage 109A.

Before the photoresist pattern 112 is formed, a thin film with high etching selectivity with respect to the polysilicon layer 111 may be deposited on the polysilicon layer 111.

Thereafter, an etching process is performed using the photoresist pattern 112 as an etch mask to selectively etch the polysilicon layer 111. The etching process is a dry etching process. Thus, at least one etching hole 113 exposing a portion of an edge of the etching passage 109A is formed, and a support layer 111A of the polysilicon layer 111 is formed. Thereafter, referring to FIG. 3I, a strip process is performed to remove the photoresist pattern 112.

Thereafter, a wet etching solution or a gas phase etching gas is introduced through the etching hole 113, thereby removing the LTO layer of the etching passage 109A and the thermal $SiO_2$ layer 106 serving as a sacrificial layer. Accordingly, a cavity 114 is formed in the region 107 where the cavity is to be formed. The fine pores 108 in the thermal $SiO_2$ layer allow the etching solution or gas to be easily infiltrated up to a lower portion of the thermal $SiO_2$ layer 106 by a capillary force or diffusion process.

For example, in the case of a wet etching process for a micro gas sensor having a diameter of approximately 200 μm and a depth of approximately 5 μm to approximately 6 μm and including four etching holes 113, the silicon substrate 101 is dipped in a concentrated HF solution—an 49% HF solution diluted with $NH_4F$— for about 40 minutes to about 60 minutes, thereby rapidly etching the thermal $SiO_2$ layer 106 and the LTO layer of the etching passage 109A in the region 107 where a vacuum cavity is to be formed.

Thereafter, the silicon substrate 101 is dipped in a 2:1 BHF solution for more than one hour, thereby removing etch residues that may be generated during an etching reaction. Also, if a gas phase etching (GPE) process is performed, the silicon substrate 101 is loaded to a gas phase etching equipment, and a temperature of the substrate 101 is adjusted to approximately 22° C. to approximately 35° C., and pressure of a reactor is adjusted to a range of approximately 10 Torr to approximately 100 Torr. Then, anhydrous HF process gas are provided into the etching equipment to remove the thermal $SiO_2$ layer 106 and the LTO layer of the etching passage 109A through an HF etching reaction in a gas phase.

If the wet etching process and the gas phase etching process described above are performed together during the process of removing the thermal $SiO_2$ layer 106 and the LTO layer of the etching passage 109A, improved etching results can be obtained. Also, if the width of the fine pore 108 is widened or the number of etching holes 113 and branching etching passages 109A is increased, a HF deep-out time can be shortened.

Through the method described above, an air cavity 114 on which the support layer 111A of the polysilicon layer is formed in the silicon substrate 101.

The air cavity 114 has a random plane shape such as a circle, a semicircle, an oval, a lozenge, a parallelogram, a trapezoid, a triangle, a quadrangle, a hexagon, and octagon. Also, the air cavity 114 has a diameter (b in FIG. 1), a surface dimension, or a width ranging from approximately 1 μm to 10 mm on the plane.

Also, the air cavity 114 has a depth (a in FIG. 1) ranging from 1 μm to hundreds of micrometers, preferably from approximately 1 μm to approximately 900 μm from an upper portion of the silicon substrate 101.

Thereafter, as shown in FIG. 3J, the silicon substrate 101 including the air cavity 114 is heated in a vacuum furnace or a furnace at a temperature ranging from approximately 400° C. to 500° C., preferably 450° C., in $N_2$ atmosphere for at least 30 minutes, preferably for about 30 minutes to 1 hour, thereby removing moistures remaining on a surface of the silicon substrate 101 including the cavity 114.

Thereafter, a sealing layer 115 is deposited on the silicon substrate 101 including the air cavity 114 to seal the air cavity 114. Since the deposition process of the sealing layer 115 is performed in a vacuum environment, the air inside the air cavity 114 is discharged, simultaneously depositing both sides 115A of the sealing layer 115 inside the etching passage 109A to be adhered to each other.

Accordingly, sealing portions 115A are formed, thereby completing a structure of a sealed vacuum cavity 114A. The sealing layer 115 may serve to electrically insulate the support layer 111A from a micro heater 117A of FIG. 3K.

The sealing layer 115 may be formed of an electrically insulating material. In this case, the insulator such as a $SiO_2$ layer, a $Si_3N_4$ layer, or an un-doped polysilicon layer is deposited as a single layer, a stacked layer or multiple layers with a thickness of at least 4000 Å, preferably from 4000 521 to approximately 6000 Å.

Besides, for the sealing layer 115, a borophosphosilicate glass (BPSG) layer, a phosphosilicate glass (PSG) layer, a spin-on-glass (SOG) layer, or a tetraethyl orthosilicate (TEOS)-based SiO$_2$ layer may be used.

Thereafter, referring to FIG. 3K, a polysilicon layer (not shown) used as a micro heater is deposited on the sealing layer 115. The polysilicon layer is deposited with a thickness ranging from approximately 2000 Å to approximately 8000 Å by an LPCVD method. The reason why the micro heater is formed using the polysilicon layer is that the polysilicon layer can be easily formed by a CMOS semiconductor manufacturing technology, and achieve low power consumption, a fast response speed, and stable operational characteristics.

Thereafter, for high electrical conductivity, the polysilicon layer is n$^+$-doped using a n-type doping source in a furnace at a temperature ranging from approximately 850° C. to approximately 900° C. in a nitrogen and oxygen atmosphere. POCl$_3$ is used as the doping source, and the doping is performed by diffusing POCl$_3$ into the polysilicon layer and then dipping the resulting object in BHF for about one minute to remove thin residue on a surface. Alternatively, a P$^+$ source such as boron may be used for doping, or a thermal treatment is performed after B, BF$_2$, P, As and Sb ion implantation. Hereinafter, description will be made on the case of n$^+$ doping.

Thereafter, a photoresist layer is applied on the n$^+$-doped polysilicon layer, and then exposure and development processes using a photo mask are sequentially performed to form a photoresist pattern 116 defining a micro heater.

Then, an etching process is performed on the n$^+$-doped polysilicon layer by using the photoresist pattern 116 as an etch mask, thereby forming a micro heater 117A on the sealing layer 115 corresponding to the vacuum cavity 114A. The micro heater 117A is not limited to a specific shape such as a circle, and may be formed into various shapes. Reference number 117B indicates an integral portion with the micro heater 117A, which is connected with a metallization line 122C through a contact hole 120 to be formed later. Hereinafter, the portion 117B is called a 'contact portion'.

Since the micro heater 117A is formed of the doped polysilicon layer, the process is compatible with a general semiconductor manufacturing process, while thermal durability against to a high temperature required by the micro gas sensor is ensured. Since the vacuum cavity 114A is disposed between the micro heater 117A and the silicon substrate 101, heat loss to a lower portion of the silicon substrate 101 can be greatly reduced, and a gas sensitive layer 129A of FIG. 3R can be heated to a high temperature even if a low voltage or current is applied to the micro heater 117A.

Also, since thermal mass of the structure is reduced, the gas sensitive layer 129A can be heated or cooled rapidly. As the width or depth of the vacuum cavity 114A is wider or deeper, relative to the size of the micro heater 117A, heat loss is reduced.

Instead of the doped polysilicon layer, the micro heater 117A may be formed of metal such as platinum (Pt) or one of materials including such metal.

Then, referring to FIG. 3L, a strip process is performed to remove the photoresist pattern 116. Thereafter, a washing process is performed.

Then, an interlayer dielectric layer 118 is deposited along a height difference on an upper portion of the silicon substrate 101 including the micro heater 117A. As for the interlayer dielectric layer 118, a single layer, a stacked layer, or multiple layers of e.g., a SiO$_2$ layer or a Si$_3$N$_4$ layer are deposited with a thickness ranging from approximately 3000 Å to approximately 8000 Å by an LPCVD method or a PECVD method. Besides, modified SiO$_2$ layers such as a BPSG layer, a PSG layer, and an SOG layer may be combined with various thicknesses, so that the interlayer dielectric layer 118 with improved flatness can be formed.

Thereafter, a photoresist layer is applied on the interlayer dielectric layer 118, and then exposure and development processes using a photo mask are sequentially performed to form a photoresist pattern 119 exposing the contact portions 117B.

Thereafter, an etching process is performed by using the photoresist pattern 119 as an etch mask to etch the interlayer dielectric layer 118. The etching process may be a dry etching process or a wet etching process. Thus, two contact holes 120 respectively exposing the contact portions 117B, i.e., a part of the micro heater 117A are formed. Through the contact hole 120 formed in such a manner, the metallization line 122C and the contact portion 117B are connected with each other.

Referring to FIG. 3M, a strip process is performed to remove the photoresist pattern 119.

Then, a washing process is performed. The washing process may be performed for about one minute by using a dilute BHF solution in order to remove a natural silicon oxide layer formed on an interface of the contact portion 117B exposed through the contact hole 120, and to reduce inclination of an upper end portion of the interlayer dielectric layer 118 surrounding the contact hole 120.

Thereafter, a photoresist layer is applied on the interlayer dielectric layer 118, and exposure and development processes using a photo mask are sequentially performed to form a photoresist pattern 121. The photoresist pattern 121 is formed through an image reversal process using a photo mask, and has a structure opened at a region where electrodes 122A and 122B of FIG. 3N are to be formed, and at a region where a metallization line 122C of FIG. 3N is to be formed.

Thereafter, a metal layer 122 used as a material of the metallization line 122C and the pair of electrodes 122A and 122B separated from each other is deposited on the photoresist pattern 121. The metal layer 122 is formed of platinum (Pt) or a staked layer including at least platinum, for example, a Ti/Pt stacked layer or a TiW/Pt stacked layer. Specifically, the metal layer 122 is formed as a stacked layer of Ti/Pt or TiW/Pt by sequentially depositing a base layer of Ti or TiW having a thickness ranging from approximately 100 Å to approximately 1000 Å, and a Pt layer having a thickness ranging from approximately 1000 Å to approximately 3000 Å by a sputtering method or an electron-beam evaporation deposition method. This is because the metal layer 122 must not be deformed by heat, and must have excellent material characteristics bearing a high current density since the metallization line 122C and the electrodes 122A and 122B contact the micro heater 117A heating a gas sensitive layer 129A at a temperature range between approximately 100° C. to approximately 600° C. or is indirectly heated thereby. A general aluminum-based wire cannot satisfy this requirement, and platinum may be used, which is compatible in a general very large scale integration (VLSI) process.

Then, referring to FIG. 3N, a lift-off process is performed to remove the photoresist pattern 121, thereby forming the pair of electrodes 122A and 122B separated from each other, and the metallization line 122C. The electrodes 122A and 122B have an interdigitated array (IDA) structure, each having at least one branching finger. Each of the electrodes 122A and 122B has a quadrangular or circular comb shape. However, the electrodes 122A and 122B are not limited to the aforementioned shape.

A process of forming the pair of electrodes 122A and 122B and the metallization line 122C is not limited to the lift-off process, and they can be formed through a dry etching process or a wet etching process.

Besides Ti or TiW, the Pt layer may be combined with another conductive layer as a lower base layer, which has metal such as TiN, $TiO_2$, Ta, TaN, Ti/Ni, and Cr as a base material. The base metal layer improves adhesiveness crystalline orientation in forming the Pt layer.

Also, the base metal layer serves as a barrier layer that prevents an element of the gas sensitive layer 129A formed on the pair of separated electrodes 122A and 122B from being diffused to a peripheral portion during or after a reaction with the Pt layer and the polysilicon layer of the micro heater 117A when high-temperature heating is performed. The metallization line 122C and the pair of electrodes 122A and 122B are formed of platinum (Pt) or one of materials including Pt.

Thereafter, an interlayer dielectric layer 123 is deposited on the silicon substrate 101 including the metallization line 122C and the pair of electrodes 122A and 122B, and serves as an uppermost protection insulation layer. As for the interlayer dielectric layer 123, an insulator such as a $SiO_2$ layer, a $Si_3N_4$ layer, or an un-doped polysilicon layer is deposited as a single layer, a stacked layer or multiple layers with a thickness ranging from approximately 3000 Å to approximately 20000 Å by using an LPCVD method or a PECVD method. Besides, a BPSG layer, a PSG layer, a SOG layer, or a TEOS-based $SiO_2$ layer may be used for the interlayer dielectric layer 123.

Referring to FIG. 3O, a photoresist layer is applied on the interlayer dielectric layer 123, and exposure and development processes using a photo mask are sequentially performed to form a photoresist pattern 124. The photoresist pattern 124 has a structure opened at a region 125A where the gas sensitive layer 129A is to be formed and at a portion where a pad part 125B connected with the metallization line 122C is to be formed. The pad part 125B becomes a portion of the metallization line 122C.

Thereafter, an etching process is performed on the interlayer dielectric layer 123 by using the photoresist pattern 124 as an etch mask, thereby forming an interlayer dielectric pattern 123A defining the region 125A where the gas sensitive layer 129A is to be formed, and the pad part 125B connected with the metallization line 122C. Total four pad parts 125B are formed at upper, lower, left and right portions, respectively. The two upper and lower pad parts 125B (see FIGS. 1 and 2) are respectively connected to the electrodes 122A and 122B separated from each other.

Referring to FIG. 3P, a strip process is performed to remove the photoresist pattern 124.

Then, a washing process is performed.

Thereafter, a photoresist pattern 126 exposing only the pad parts 125B is formed through an image reversal process.

Then, a gold (Au) layer 127 is deposited along a height difference on the silicon substrate 101 including the photoresist pattern 126. The gold layer 127 acts as an auxiliary conductive layer of the pad part 125B formed for stable connection of an external wire. In general, since the micro gas sensor may be used in a harsh environment of high temperature and humidity, or toxic gases, an aluminum-based pad of the general VLSI process cannot be used herein. Thus, the metal layer having excellent resistance against oxidation and corrosion may be added to a top surface of the pad part 125B.

Thereafter, referring to FIG. 3Q, a lift-off process is performed to remove the photoresist pattern 126. Thus, the gold layer 127 on the photoresist pattern 126 is removed simultaneously with the photoresist pattern 126, so that the gold layer 127 remains only on the pad part 125B formed integrally with the metallization line 122C. Hereinafter, the remaining gold layer 127 is called an auxiliary conductive layer.

Thereafter, a washing process is performed.

The process of forming the auxiliary conductive layer 127 described with reference to FIGS. 3O to 3Q may be omitted for process simplicity.

Thereafter, a photoresist pattern 128 exposing a region 125A where the gas sensitive layer 129A is to be formed.

Then, a material 129 for a gas sensitive layer is formed along a height difference on the silicon substrate 101 including the photoresist pattern 128. The material 129 for the gas sensitive layer is deposited with a thickness ranging from approximately 500 Å to 10000 Å by an electron-beam evaporation deposition method, a sputtering method, or a pulsed layer deposition method.

As another deposition method, a sol-gel method, a chemical vapor deposition (CVD) method, a spray coating method, a dip-coating method, or a screen-printing method may be used. A range of the layer thickness may expand according to a desired sensitivity range of the micro gas sensor device. Also, the material 129 for the gas sensitive layer is metal oxide such as $SnO_2$, ZnO, $WO_3$, $In_2O_3$, $Ga_2O_3$, $Fe_2O_3$, $TiO_2$, NiO, or $MoO_3$, or a doped film of the metal oxide.

Any thin film material undergoing a change in electrical characteristics according to gas concentration can be used. Examples of the material include a nanotube or a nanowire of carbon, silicon or metal, or an array thereof. The thin film material is not limited to a specific material, and may be any one of metal oxide, metal, a semiconductor, and a mixture thereof.

Referring to FIG. 3R, a lift-off process is performed to remove the photoresist pattern 128. The material 129 for the gas sensitive layer on the photoresist pattern 128 is removed simultaneously with the photoresist pattern 128, thereby forming the gas sensitive layer 129A covering the pair of electrodes 122A and 122B. If the gas sensitive layer 129A is formed of metal oxide, a final thickness thereof may range from approximately 500 Å to approximately 5000 Å.

Although the gas sensitive layer 129A is formed through the lift-off process in the above description, the gas sensitive layer 129A may be formed through, e.g., a dry etching process or a wet etching process. Alternatively, a shadow mask which is previously prepared is mounted on the silicon substrate 101, and is aligned in a region where the gas sensitive layer 129A is to be formed, thereby forming the gas sensitive layer 129A without operations of the photoresist pattern.

Thereafter, to stabilize the gas sensitive layer 129A, a heat treatment is performed on the gas sensitive layer 129A in a furnace in oxygen atmosphere, e.g., in $O_2$, $O_3$ or $N_2O$ atmosphere or in the air. Alternatively, a rapid thermal processing (RTP) process may be additionally performed.

Embodiment 2

Figure 2A:
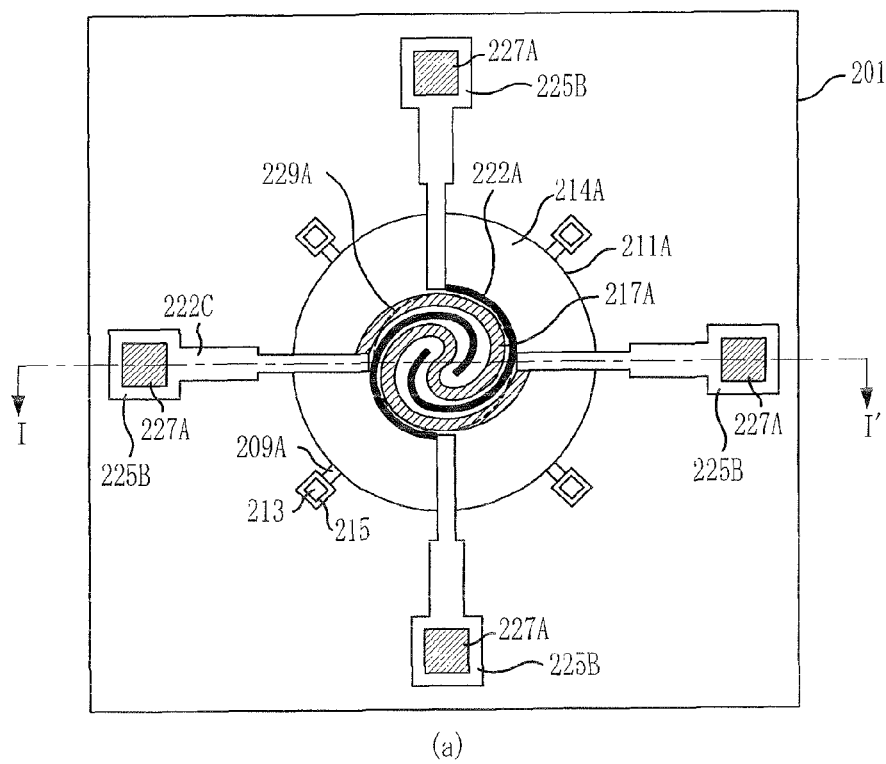
FIG. 2A is a plane view of a micro gas sensor in accordance with a second embodiment of the present invention.
Figure 2B:
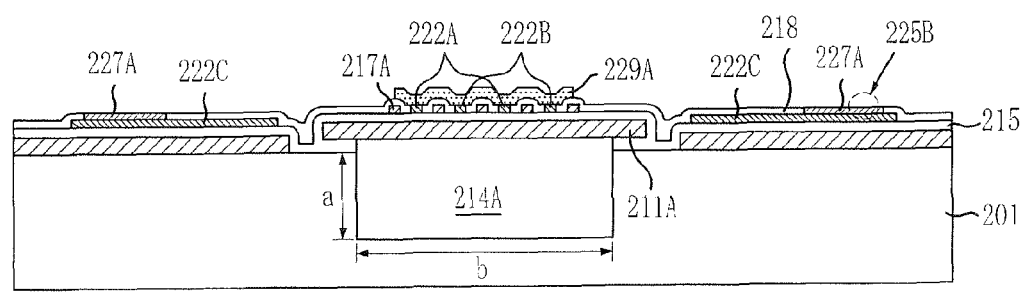
FIG. 2B is a cross-sectional view taken along line I-I' of FIG. 2A.

FIG. 2A is a plane view of a micro gas sensor in accordance with a second embodiment of the present invention, and FIG. 2B is a cross-sectional view taken along line I-I' of FIG. 2A.

Referring to FIGS. 2A and 2B, the micro gas sensor in accordance with the second embodiment of the present invention is similar to the micro gas sensor in accordance with the first embodiment of the present invention, except that a micro heater 217A and electrodes 222A and 222B are formed on the same plane. In the micro gas sensor of FIG. 1 in accordance with the first embodiment of the present invention, the micro heater 117A and the electrodes 122A and 122B are formed on different planes.

Unlike the micro gas sensor of FIG. 1A including the insulation layer 118 for insulating the electrodes 122A and 122B from the micro heater 117A, an insulation layer is unnecessary for the micro gas sensor in accordance with the second embodiment of the present invention, which includes the micro heater 217A and the electrodes 222A and 222B on the same plane. As compared to the first embodiment of the present invention, since a process of forming the insulation layer 118 can be omitted, an entire process can be simplified, and a manufacturing cost can also be reduced.

Figure 4A:
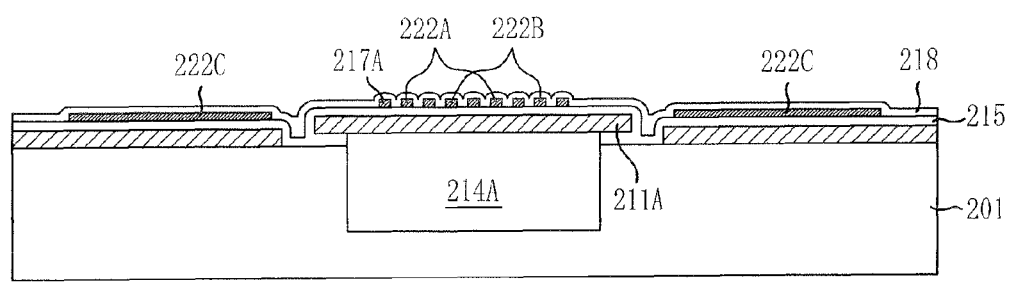
FIGS. 4A and 4B are cross-sectional views of a method for manufacturing the micro gas sensor in accordance with the second embodiment of the present invention.
Figure 4B:
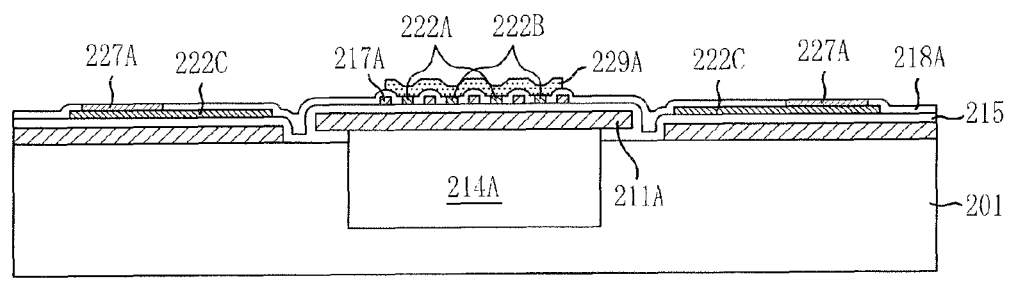

FIGS. 4A and 4B are cross-sectional views sequentially showing a method for manufacturing the micro gas sensor in accordance with the second embodiment of the present invention.

First, a process shown in FIG. 4A corresponds to the processes shown in FIGS. 3K to 3N of the method for manufacturing the micro gas sensor in accordance with the first embodiment of the present invention. That is, the process of FIG. 4A corresponds to a subsequent process of the process of FIG. 3J of the first embodiment of the present invention. Processes before the process of FIG. 4A are the same as those shown in FIGS. 3A to 3J.

Referring to FIG. 4A, a metal layer used as a micro heater 217A and electrodes 222A and 222B is deposited on a silicon substrate 201 including a support layer 211A, a vacuum cavity 214A, and a sealing layer 215. The metal layer may include platinum as a base material, which is compatible in a semiconductor process. This is because the metal layer must not be deformed by heat and must have excellent material characteristics bearing a high current density since portions where the metallization lines 222C and the electrodes 222A and 222B are formed contact with the micro heater 217A heating a gas sensitive layer 229A within a temperature range of approximately 100° C. to approximately 600° C., or are heated indirectly thereby. A general aluminum-based semiconductor wire cannot satisfy the characteristics.

Specifically, the metal layer is formed of platinum or as a stacked layer including at least platinum, for example, a stacked layer of Ti/Pt or TiW/Pt. A base layer of Ti or TiW having a thickness ranging from approximately 100 Å to approximately 1000 Å, and a Pt layer having a thickness ranging from approximately 1000 Å to approximately 3000 Å are sequentially deposited by using a sputtering method or an electron-beam evaporation deposition method, thereby forming the stacked layer of Ti/Pt or TiW/Pt.

Thereafter, the metal layer is etched through a dry etching process or a wet etching process to form the micro heater 217A, the pair of electrodes 222A and 222B separated from each other, and a metallization line 222C.

The micro heater 217A, the electrodes 222A and 222B, and the metallization line 222C are formed through a lift-off process. In this case, before the metal layer is deposited, a photoresist pattern (not shown) opened at a region where the micro heater 217A, the electrodes 222A and 222B, and the metallization line 222C are to be formed is provided. Thereafter, the metal layer is deposited thereon, and then the photoresist pattern is removed.

Besides Ti or TiW, another conductive layer including metal such as TiN, TiO$_2$, Ta, TaN, Ti/Ni, and Cr may be used for the base layer under the Pt layer.

Thereafter, an interlayer dielectric layer 218 is formed to cover the micro heater 217A, the electrodes 222A and 222B, and the metallization line 222C. As for the interlayer dielectric layer 218, a single layer, a stacked layer or multiple layers of an insulator such as a SiO$_2$ layer, a Si$_3$N$_4$ layer, and an un-doped polysilicon layer is deposited with a thickness ranging from approximately 3000 Å to approximately 8000 Å. Besides, a BPSG layer, a PSG layer, a SOG layer, or a TEOS-based SiO$_2$ layer may be used for the interlayer dielectric layer 218.

Referring to FIG. 4A, a photoresist pattern (not shown) is formed on the interlayer dielectric layer 218. The photoresist pattern has a structure exposing a part of the metallization line 222C.

Thereafter, an etching process is performed by using the photoresist pattern as an etch mask to etch the interlayer dielectric layer 218.

Referring to FIG. 4B, an interlayer dielectric pattern 218A exposing a part of the metallization line 222C is formed. Thereafter, a gold layer is deposited on the substrate 201 including the exposed metallization line 222C.

Then, a lift-off process is performed to remove the photoresist pattern, thereby forming a pad 227A on the exposed metallization line 222C.

Thereafter, the gas sensitive layer 229A is formed to cover the pair of electrodes 222A and 222B separated from each other.

In accordance with the second embodiment of the present invention, the micro heater 217A and the electrodes 222A and 222B are formed on the same plane, and thus two mask manufacturing processes are omitted as compared to the first embodiment of the present invention. Accordingly two masks can be saved, thereby simplifying the manufacturing process. For example, in the second embodiment in accordance with the current embodiment, 6 or 7 masks are used.

Hereinafter, comparison of a die size will be made between a micro gas sensor in accordance with the first or second embodiment of the present invention and a typical micro gas sensor bulk-micromachined through existing wet silicon etching.

Figure 5:
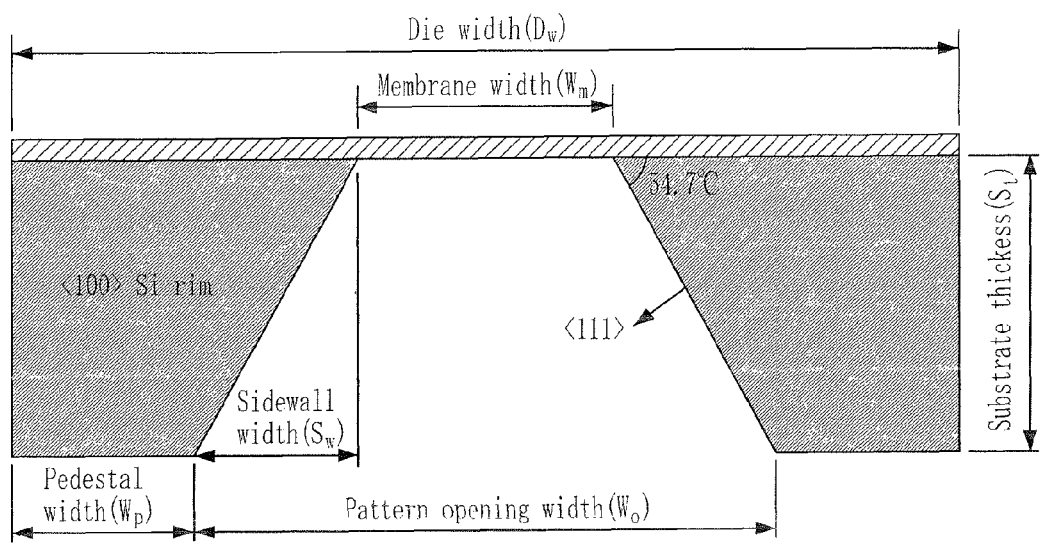
FIG. 5 is a cross-sectional view showing a part of a typical bulk-micromachined gas sensor.

Referring to FIG. 5, as for the typical micro gas sensor bulk-micromachined through wet silicon etching, a silicon substrate with <100> crystal direction, which is commonly used, is anisotropically etched as deep as a substrate thickness S$_t$ through a square pattern opening having a width W$_o$ and formed in a back surface of the silicon substrate by using a wet silicon etching solution such as potassium hydroxide (KOH), tetramethylammonium hydroxide (TMAH), or ethylenediamine pyrocatechol (EDP), and a membrane having a width W$_m$ is manufactured, which is made of the previously deposited insulation layer on a front side of the substrate.

The pattern opening W$_o$ in the back side of the substrate must meet geometrical specifications of the following equation 1, and a die width D$_w$ of a device is determined by the following equation 2.

$$W_o \geq W_m + \sqrt{2} S_t \qquad \text{Eq. 1}$$

$$D_w = W_o + 2W_p \qquad \text{Eq. 2}$$

Accordingly, the die width D, of the micro gas sensor bulk-micromachined through wet silicon etching must be designed to be sufficiently wide in due consideration of a sidewall width S$_w$. After all, this is related to the substrate thickness, the pattern opening width, and a pedestal width W$_p$, which is a width of a lower portion of a silicon rim.

When the final membrane is formed, an etch front of <111> crystal direction, and an open cavity with an angle of 54.7° are simultaneously formed. In general, the membrane has a quadrangular shape, and if the membrane shape is not the quadrangle, a pattern for etching compensation of a corner portion must be added, which causes difficulties in the manufacturing process.

Figure 6:
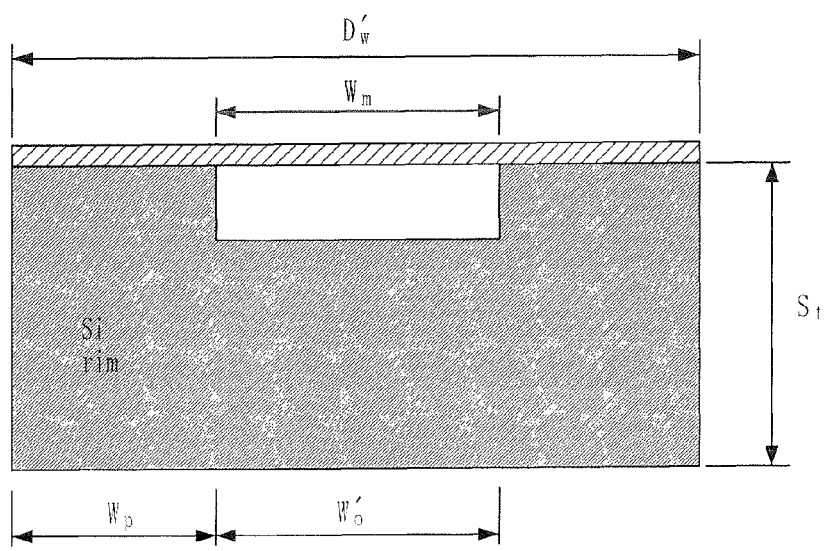
FIG. 6 is a cross-sectional view showing a part of a micro gas sensor manufactured in accordance with an embodiment of the present invention.

FIG. 6 is a cross-sectional view of a die of a micro gas sensor in accordance with the first or second embodiment of the present invention. Hereinafter, a structure of the micro gas sensor in accordance with the first or second embodiment of the present invention will now be described with reference to FIG. 6 in comparison with the structure of the typical micro gas sensor.

In the present invention, a vacuum cavity is formed in a front side of a silicon substrate through dry etching and sealing processes. Accordingly, a membrane with the buried vacuum cavity having a random shape is advantageously manufactured without being affected by the substrate thickness $S_t$ and the pedestal width $W_p$ due to the crystal direction of silicon. Accordingly, the geometrical specifications of the micro gas sensor manufactured in the aforementioned manner have relationships of the following equations 3 and 4.

$$W_o' \sim W_m \qquad \text{Eq. 3}$$

$$D_w' = W_o' + 2W_p \qquad \text{Eq. 4}$$

where $W_o'$ and $D_w'$ denote a pattern opening width observed from a back side of the substrate, and a die width, respectively.

In accordance with the present invention, when the same cavity size is ensured, the die size of the micro gas sensor decreases. Thus, the total number of dies that can be obtained from a given wafer diameter increases, and thus a package size, a process defect density and drift decrease, thereby improving device quality.

Also, the decrease in final package size can contribute to remarkably lowering a device manufacturing cost. For example, on the assumption that a silicon substrate thickness, a membrane width, and a pedestal width are approximately 400 μm, approximately 1500 μm, and approximately 300 μm, respectively in both dies of FIGS. 5 and 6, a die width of FIG. 6 is approximately 2100 μm, which is smaller than that of FIG. 5 by about 21%.

When this is applied to an area of a quadrangular die, the device size is decreased by about 38% as compared to that of FIG. 5.

Unlike the typical method for manufacturing the micro gas sensor bulk-micromachined mainly through wet silicon etching from a back surface of the substrate, the method for manufacturing the micro gas sensor in accordance with the embodiments of the present invention mainly uses surface micromachining through a semiconductor thin-film process performed on a front side of the substrate. Accordingly, a micro gas sensor with a compact size can be precisely mass-produced at low cost.

Figure 7:
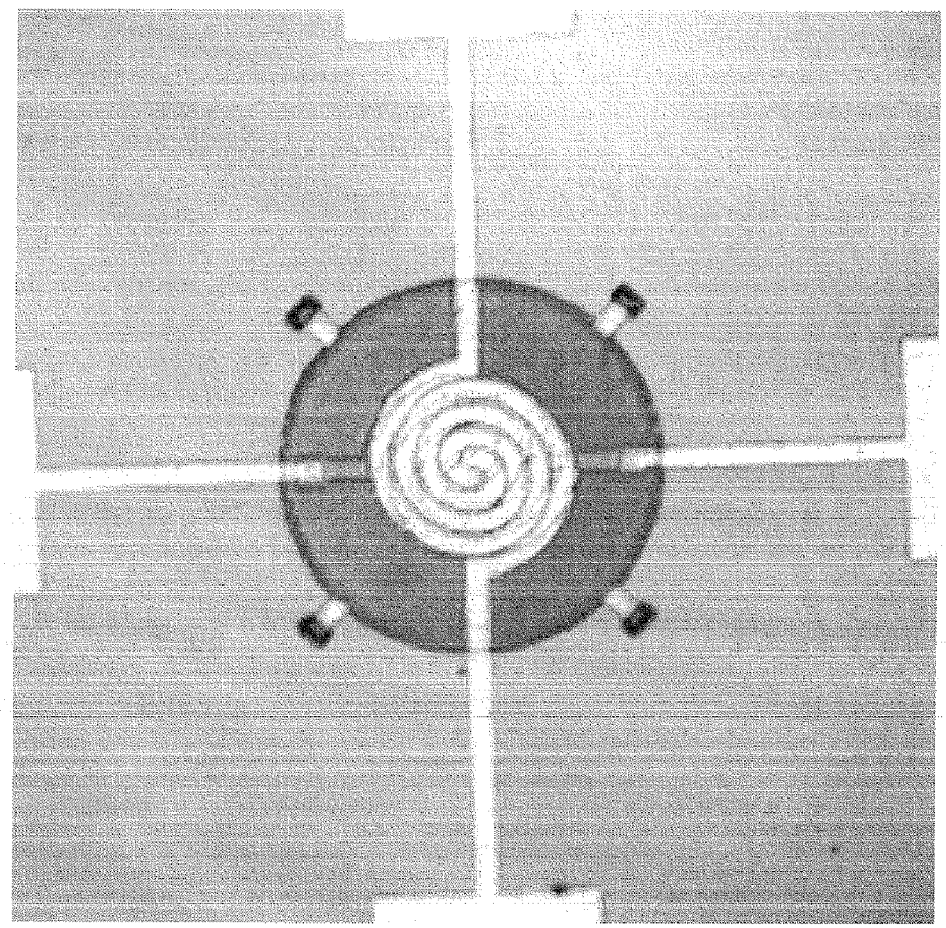
FIG. 7 is an image of an actual micro gas sensor manufactured in accordance with an embodiment of the present invention.

FIG. 7 is an image of a micro gas sensor manufactured by the manufacturing method according to the first and second embodiments of the present invention. FIG. 7 shows satisfactory production of a circular vacuum cavity having a diameter of approximately 200 μm and buried downwardly within the silicon substrate in a depth direction, a support layer of a polysilicon layer thereon, a micro heater of a polysilicon layer having a double spiral shape and formed on a sealing layer, and a pair of Pt electrodes that are separated from each other with an insulation layer therebetween. Also, in FIG. 7, a state before formation of a gas sensitive layer is shown, and four etching passages and four etching holes are used.

In accordance with the present invention, power consumption of the micro gas sensor can be reduced. Also, the gas sensitive layer of the micro gas sensor can be heated or cooled at a high speed. In accordance with the present invention, temperature uniformity of the micro gas sensor can be improved, and the micro gas sensor has durability against thermal impact and mechanical impact applied from the outside.

Also, in accordance with the present invention, a height difference of the micro gas sensor is minimized so that an influence of dust particles introduced into the micro gas sensor structure is prevented, or flow therearound is not disturbed, thereby achieving high measurement precision. Besides, in accordance with the present invention, miniaturization and low cost are achieved through a semiconductor batch process, so that the micro gas sensor can be mass-produced.

The present application contains subject matter related to Korean Patent Application No. 10-2006-0123686, filed in the Korean Intellectual Property Office on Dec. 7, 2006, the entire contents of which is incorporated herein by reference.

While the present invention has been described with respect to the specific embodiments, it will be apparent to those skilled in the art that various changes and modifications may be made without departing from the spirit and scope of the invention as defined in the following claims.

What is claimed is:

1. A micro gas sensor, comprising:
a vacuum cavity disposed in a substrate;
a support layer having a first part covering the vacuum cavity and a second part in contact with the substrate, an upper surface of the first part being disposed at a level higher than a level at which an upper surface of the second part is disposed;
a passage between the substrate and the first part of the support layer, the passage branching outwardly from an edge of the vacuum cavity, the passage having an inner end adjacent to the cavity and an outer end adjacent an outer periphery of the first part of the support layer;
a sealing layer deposited to fill the passage, thereby sealing the vacuum cavity, the sealing layer being further disposed on the upper surface of the first part of the support layer and the upper surface of the second part of the support layer, the sealing layer entirely filling and closing the inner end of the passage;
a micro heater disposed on the sealing layer;
a plurality of electrodes insulated from the micro heater; and
a gas sensitive layer covering the electrodes.

2. The micro gas sensor of claim 1, wherein the electrodes are formed over the micro heater.

3. The micro gas sensor of claim 2, further comprising an insulation layer insulating the electrodes from the micro heater.

4. The micro gas sensor of claim 3, wherein the insulation layer is formed of an electrically insulating material.

5. The micro gas sensor of claim 1, wherein the electrodes are formed on the same plane as the micro heater.

6. The micro gas sensor of claim 1, wherein the vacuum cavity has a plane structure with any one shape of a circle, a semicircle, an oval, a lozenge, a parallelogram, a trapezoid, a triangle, a quadrangle, a hexagon, and an octagon.

7. The micro gas sensor of claim 1, wherein the vacuum cavity has a diameter, a surface dimension, or a width ranging from 1 μm to 10 mm on a plane.

8. The micro gas sensor of claim 1, wherein the vacuum cavity is buried with a depth ranging from 1 μm to 900 μm from the top surface of the substrate.

9. The micro gas sensor of claim 1, wherein the support layer is formed of a polysilicon layer, and
wherein the lower surface of the first part of the support layer is disposed at a level higher than a level at which the top surface of the substrate is disposed.

10. The micro gas sensor of claim 1, wherein the support layer has a thickness ranging from 1 μm to 20 μm, the thickness of the first part of the support layer is substantially the same as the thickness of the second part of the support layer, and wherein the lower surface of the first part of the support layer is disposed at a level higher than a level at which the top surface of the substrate is disposed.

11. The micro gas sensor of claim 1, wherein the micro heater is formed of an impurity-doped polysilicon layer.

12. The micro gas sensor of claim 1, wherein the micro heater is formed of a single layer of platinum, or a stack of multiple layers including at least platinum.

13. The micro gas sensor of claim 1, wherein the electrodes are separated from each other, and have an interdigitated array (IDA) structure.

14. The micro gas sensor of claim 1, wherein the electrodes each has at least one branching finger.

15. The micro gas sensor of claim 1, wherein the electrodes are formed of a single layer of platinum, or a stack of multiple layers including at least platinum.

16. The micro gas sensor of claim 1, wherein the gas sensitive layer is formed of a metal, a semiconductor, or metal oxide.

17. The micro gas sensor of claim 1, further comprising a plurality of metallization lines connected with the micro heater.

18. The micro gas sensor of claim 17, wherein the metallization line is formed integrally with the micro heater.

19. The micro gas sensor of claim 18, further comprising a pad formed on a portion of the metallization line.

20. The micro gas sensor of claim 1, further comprising a plurality of metallization lines respectively connected to the electrodes.

21. The micro gas sensor of claim 20, wherein the metallization line is formed integrally with the electrode.

22. The micro gas sensor of claim 21, further comprising a pad formed on a portion of the metallization line.

23. The micro gas sensor of claim 1, wherein the sealing layer is formed of an electrically insulating material.

24. The micro gas sensor of claim 1, wherein a side of the sealing layer is disposed adjacent to the inner end of the passage.

* * * * *